United States Patent
Kimoto et al.

(10) Patent No.: US 10,261,027 B2
(45) Date of Patent: Apr. 16, 2019

(54) INSPECTION DEVICE

(71) Applicant: Hitachi High-Technologies Corporation, Minato-ku, Tokyo (JP)

(72) Inventors: Yoshio Kimoto, Tokyo (JP); Akira Hamamatsu, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 15/569,503

(22) PCT Filed: May 26, 2015

(86) PCT No.: PCT/JP2015/065064
§ 371 (c)(1),
(2) Date: Oct. 26, 2017

(87) PCT Pub. No.: WO2016/189650
PCT Pub. Date: Dec. 1, 2016

(65) Prior Publication Data
US 2018/0088055 A1    Mar. 29, 2018

(51) Int. Cl.
*G01N 21/47* (2006.01)
*G01N 21/88* (2006.01)
*G01N 21/95* (2006.01)

(52) U.S. Cl.
CPC ......... *G01N 21/8806* (2013.01); *G01N 21/47* (2013.01); *G01N 21/9501* (2013.01);
(Continued)

(58) Field of Classification Search
CPC .............. G01N 21/8806; G01N 21/47
(Continued)

(56) References Cited

U.S. PATENT DOCUMENTS 5,034,679 A * 7/1991 Henderson ............. G01D 5/344
324/117 R
6,134,011 A * 10/2000 Klein ....................... G01J 4/04
250/225

(Continued)

FOREIGN PATENT DOCUMENTS

| JP | 2007-225432 A | 9/2007 |
| JP | 2010-529461 A | 8/2010 |
| JP | 2015-28457 A | 2/2015 |

OTHER PUBLICATIONS

International Search Report (PCT/ISA/210) issued in PCT Application No. PCT/JP2015/065064 dated Aug. 18, 2015 with English translation (Two (2) pages).
(Continued)

Primary Examiner — Roy M Punnoose
(74) Attorney, Agent, or Firm — Crowell & Moring LLP

(57) ABSTRACT

Proposed is an inspection device that is provided with: an illuminating optical unit that irradiates a discretionary region of a sample with light; a control unit that gives instructions to the illuminating optical unit; and at least one detection unit that detects light transmitted from the sample. The illuminating optical unit includes a light source unit that generates light, and an electrooptic element unit to which the light generated by the light source unit is inputted, and on the basis of the instructions given from the control unit, the electrooptic element unit adjusts the light to be in a desired polarization state, said light having been generated by the light source unit, and irradiates the sample with the light.

12 Claims, 9 Drawing Sheets

(52) U.S. Cl.
CPC ............... *G01N 2021/4792* (2013.01); *G01N 2021/8848* (2013.01)

(58) Field of Classification Search
USPC ........................................................ 356/369
See application file for complete search history.

(56) References Cited

U.S. PATENT DOCUMENTS

| | | | |
|---|---|---|---|
| 8,830,465 B2* | 9/2014 | Taniguchi | G01N 21/956 356/369 |
| 2008/0304069 A1* | 12/2008 | Wolters | G01N 21/4738 356/446 |
| 2009/0201483 A1* | 8/2009 | Janssens | G02B 27/28 355/71 |
| 2013/0114078 A1* | 5/2013 | Honda | G01N 21/9501 356/364 |
| 2013/0242294 A1* | 9/2013 | Taniguchi | G01N 21/956 356/237.5 |
| 2014/0268122 A1* | 9/2014 | Matsumoto | G01N 21/956 356/237.6 |
| 2015/0116702 A1* | 4/2015 | Matsumoto | G01N 21/9501 356/237.5 |

OTHER PUBLICATIONS

Japanese-language Written Opinion (PCT/ISA/237) issued in PCT Application No. PCT/JP2015/065064 dated Aug. 18, 2015 (Four (4) pages).

* cited by examiner

| POLARIZATION STATE IN OUTPUT STAGE OF ELECTRO-OPTIC DEVICE 110 | | POLARIZATION STATE IN OUTPUT STAGE OF PBS 1101 | TRANSMISSIVITY OF PBS 1101 |
|---|---|---|---|
| ↕ | P-POLARIZATION STATE | ↕ | 100% |
| ⬭ | ELLIPTICAL POLARIZATION | ↕ | 100%-50% |
| ○ | CIRCULAR POLARIZATION | ↕ | 50% |
| ⬯ | ELLIPTICAL POLARIZATION | ↕ | 0%-50% |
| ↔ | S-POLARIZATION STATE | | 0% |

INSPECTION DEVICE

TECHNICAL FIELD

The present invention relates to an inspection device that detects a defect on a specimen.

BACKGROUND ART

To improve the yield of a semiconductor manufacturing apparatus, a defect on the surface of a semiconductor wafer is detected by using a defect inspection device. With the advances in miniaturization in the semiconductor process, even a relatively small defect (having a size that is above several tens of nm) on a semiconductor wafer is required to be managed. This is because even the small defect can adverse the semiconductor process.

As an example of the defect inspection device, there is a dark field optical microscope. The dark field optical microscope detects a defect by irradiating a semiconductor wafer with light and by detecting scattered light from the defect. The dark field optical microscope can detect a defect having a size that is equal to or less than one-tenth of the wavelength of irradiation light.

Factors to determine whether a certain defect can be detected include the wavelength of illumination light, the polarization state of illumination light, the power of illumination light, the size of the spot of illumination light, the scanning method of illumination light, and the irradiation angle of illumination light. The optimum state of some of the factors is different according to the type of a semiconductor wafer and the shape of a defect. In a semiconductor manufacturing factory, an optimum inspection condition is often determined for each type of semiconductor wafer to perform inspection under the one condition.

Patent Literature 1 describes an inspection method by which a specimen is illuminated by alternately switching two illumination lights having different polarization conditions, scattered light from the specimen is detected for each of the illumination lights, and the presence or absence of a defect is determined.

CITATION LIST

Patent Literature

Patent Literature 1: Japanese Unexamined Patent Application Publication No. 2007-225432

SUMMARY OF INVENTION

Technical Problem

A certain inspection condition that is optimized for each type of semiconductor wafer is typically used in one inspection. However, various defects are present on a semiconductor wafer. Thus, the inspection condition that is optimum for the type of a certain defect can be different from the inspection condition that was used in the inspection. This can cause defect to be missed.

Accordingly, in Patent Literature 1 described above, a specimen is irradiated by alternately switching two lights having different polarization conditions by an optical switch, and scattered lights are detected by different detectors disposed according to the respective polarization conditions. However, in this method, the switching of the polarization condition by the optical switch is required. This lowers the throughput more significantly than the typical inspection.

Accordingly, an object of the present invention is to improve the throughput when inspection is performed by using a plurality of inspection parameters, such as polarization, power, and an illumination angle.

Solution to Problem

To achieve the above object, the present invention adopts the configuration described in the scope. That is, the present invention adopts the configuration in which light generated by a light source unit is adjusted to be in a desired polarization state by using an electro-optic device unit, and a specimen is irradiated with the light.

More specifically, the present invention is provided with an illuminating optical unit that irradiates a discretionary region of a specimen with light, a control unit that gives instructions to the illuminating optical unit, and at least one detection unit that detects light from the specimen. The illuminating optical unit includes a light source unit that generates light, and an electro-optic device unit to which the light generated by the light source unit is inputted. On the basis of the instructions from the control unit, the electro-optic device unit adjusts the light to be in a desired polarization state, the light having been generated by the light source unit, and irradiates the specimen with the light.

Advantageous Effects of Invention

The present invention can improve the throughput when the inspection result corresponding to a plurality of conditions is obtained in one inspection. The problem, configuration, and effect other than the above will be apparent from the description of the following embodiments.

DESCRIPTION OF EMBODIMENTS

Embodiments of the present invention will be described below with reference to the drawings. It is to be noted that the embodiments of the present invention are not limited to embodiments that will be described later, and various modifications can be made in the range of its technical idea.

(1) The Definition of Terms

The "optical inspection device" herein is referred to as a device that detects a defect on a specimen by irradiating the specimen with light. A pattern may be unrequired to be formed on the specimen.

The "specimen" herein is referred to as an object to be inspected by the optical inspection device. In particular, the "specimen" is often referred to as a semiconductor wafer.

The "defect" herein is referred to as a foreign substance and abnormality including an unpreferable shape such as a dent that are present on the surface of the specimen.

The "illumination light" herein is referred to as light that is generated by a light source of the optical inspection device and is beam-formed for irradiation onto the specimen.

The "illumination condition" herein is referred to as all the parameters that represent the state of the illumination light with which the specimen is irradiated. In particular, the "illumination condition" is often referred to as a polarization state, the angle of illumination light with respect to the specimen, and the power of illumination light.

The "spot" herein is referred to as the region of the specimen that is illuminated with the illumination light.

The "beam shape" herein is referred to as a shape that is formed by connecting certain positions at the intensity of $1/e^2$ that is a maximum intensity in the spot of the illumination light.

The "feed pitch" herein is referred to as the movement amount of translational movement in the radius direction of the specimen that is performed each time a stage allows the specimen to make one rotation.

The "track" herein is referred to as the track of the spot that can be inspected by the optical inspection device while the stage allows the specimen to make one rotation.

The "integration" herein is referred to as performing at least one of the four fundamental operations of arithmetic with respect to a plurality of obtained signals or a combination of them. In particular, the "integration" often means taking a weighted average with respect to the plurality of signals.

The "adjustment of the polarization state" herein includes, not only the switching of orthogonal polarization components, but also the varying of the rates of the orthogonal polarization components. The varying of the rates includes the switching between a plurality of polarization states in which the rates of the orthogonal polarization components are different. The varying of the rates also includes the continuous switching of the rates of the orthogonal polarization components.

(2) First Embodiment (2-1) The Configuration of a Device

Figure 1:
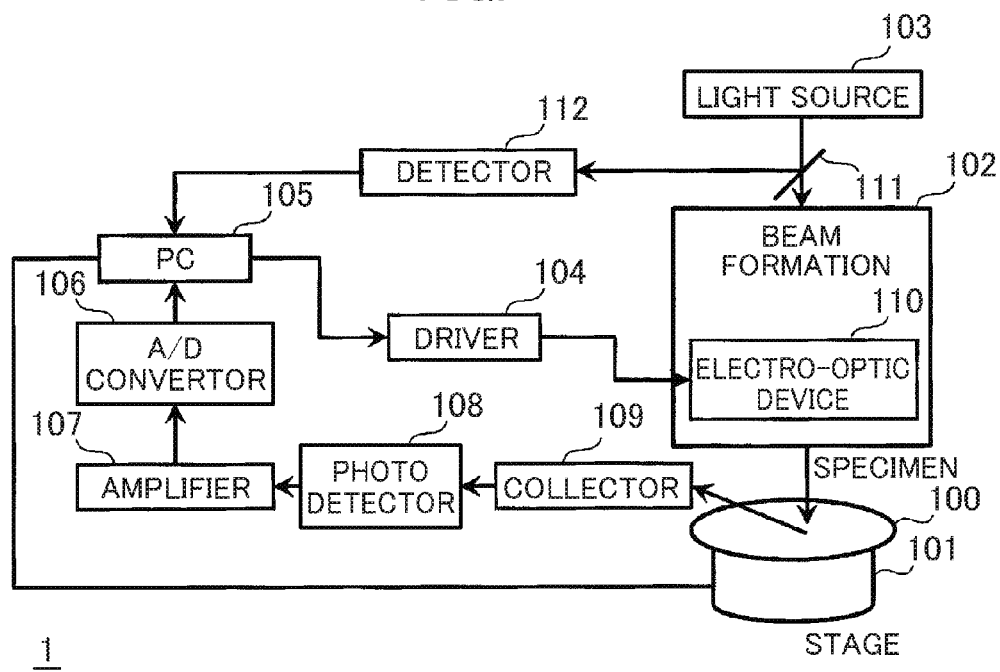
FIG. 1 is a diagram illustrating the configuration example of an inspection device according to an embodiment.

FIG. 1 illustrates the schematic configuration of an optical inspection device 1 described in this embodiment. In this embodiment, the optical inspection device 1 inspects a defect on a specimen while switching polarization conditions in a time division manner. The optical inspection device 1 has an illuminating optical system for irradiating a specimen 100 with illumination light in a spot shape, a detecting optical system that detects light from the specimen 100 to convert the light to an electric signal, a control unit that controls the operation of the optical components of the illuminating optical system and the detecting optical system, and a stage 101 for holding the specimen 100.

The illuminating optical system includes a light source 103 and a beam formation unit 102. In addition, the illuminating optical system may include a filter that can limit the wavelength of the illumination light. The filter may be a notch filter and a band pass filter.

The light source 103 may include, for example, a laser, a laser diode, a helium neon laser, an argon laser, a solid state laser, an excimer laser, a DPSS (Diode Pumped Solid State) laser, an LED, a xenon arc lamp, a gas discharge lamp, and an incandescent lamp. Light generated from the light source 103 may be near-monochromatic light or broad band light. Typically, the optical inspection device 1 often uses the near-monochromatic light as the light source. The light source 103 may provide a continuous wave or a pulse wave. Hereinafter, it is often assumed that the light source 103 provides the pulse wave.

The beam formation unit 102 includes a beam expander, an anamorphic prism, an objective lens, and an electro-optic device 110. Further, the beam formation unit 102 may include an optical device such as a mirror, a polarizing plate, a wave plate, an optical attenuator, and an elliptical mirror. The electro-optic device 110 is, for example, a Pockels cell. The electro-optic device 110 is disposed at any position on the optical path in front of and behind the beam formation unit 102 or at the midpoint of the beam formation unit 102.

In this embodiment, the illumination light from the light source 103 is split in two directions by a semitransparent mirror 111. One of the split illumination lights is inputted to the beam formation unit 102, and the other split illumination light is inputted to a detector 112. The detector 112 converts the inputted light to an electric signal according to its intensity, and outputs the electric signal as a detection signal to a PC 105. The PC 105 measures the repetition frequency of the illumination light from the detection signal inputted, and performs signal processing and control that are synchronous with this.

In this embodiment, the semitransparent mirror 111 is used for detecting the illumination light, but a configuration in which the semitransparent mirror 111 is not used is also enabled. For example, any optical device may be disposed in place of the semitransparent mirror 111, and its transmitted light or scattered light may be directly detected by the detector 112. The semitransparent mirror 111 is disposed at any position on the optical path in front of and behind the illuminating optical system or at the midpoint of the illuminating optical system. The semitransparent mirror 111 may be, for example, a plane parallel substrate, a wedge substrate, and a reflection type neutral density filter.

The detecting optical system that detects light from the specimen 100 includes a collector 109 that collects scattered light from a defect, a detector 108, a sensor output (detection signal) amplifier 107, and an A/D converter 106. Like the illuminating optical system, the detecting optical system can include one or a plurality of filters that can limit the wavelength of the light. The filter may be a notch filter and a band pass filter.

The control unit includes the processor of the PC 105, and a driver 104 that drives the electro-optic device 110. The control unit also serves as a data processing unit, the processing unit including a processor, a signal generation unit, a signal conversion unit, a signal storage unit, and a signal reception unit. The function of the control unit can also be achieved by one of hardware form and software form. The function of the control unit of the hardware form can be achieved by integrating a plurality of computing units executing processes on a wiring substrate or in a semiconductor chip or a package. The function of the control unit of the software form can be achieved through a program executing desired computation processing by a central processing unit (CPU) equipped in an apparatus configuring a system or a general purpose CPU equipped in a general purpose computer connected to a system. An existing apparatus can also be upgraded by a recording medium into which this program is recorded.

The light generated from the light source 103 is adjusted in a desired light shape and polarization state by the beam formation unit 102 and the electro-optic device 110, so that the specimen 100 is irradiated with the light. The polarization state of the light generated from the light source 103 maybe a completely polarized state or a randomly polarized state. In the optical inspection device 1, the polarization state of the light generated from the light source 103 is often a linearly polarized state.

The beam formation unit 102 can direct, to the specimen 100, the light generated from the light source 103, as an inspection beam that is suitable for a desired illumination condition (for example, polarization state and shape). For example, when the beam expander is used, the diameter of the light can be enlarged. In addition, when the anamorphic prism is used, the diameter of the light can be enlarged only in a particular direction. Further, the light can be collected by the objective lens, so that the specimen 100 is irradiated with the light.

The electro-optic device 110 changes the polarization state of the light inputted to the electro-optic device 110 according to the voltage applied from the driver 104. The electro-optic device 110 can respond to the voltage applied from the driver 104 during a time of approximately $10^{-9}$ seconds. The polarization state of the light inputted may be the completely polarized state or the randomly polarized state. When the light in the linearly polarized state is inputted to the electro-optic device 110, the electro-optic device 110 can change the polarization state of the inputted light into the polarization state of elliptical polarization, circular polarization, and linear polarization that rotates 90° from the inputted linear polarization.

The driver 104 can apply a desired voltage to the electro-optic device 110. By a control signal provided from the PC 105, the magnitude, positive and negative, and timing of the voltage applied from the driver 104 to the electro-optic device 110 are controlled. By changing the voltage applied to the electro-optic device 110, the polarization state of the light with which the specimen 100 is illuminated can be controlled.

The operation of the stage 101 is controlled by the PC 105. The stage 101 translationally moves the specimen 100 while rotating the specimen 100 held on its placing surface at high speed. This helically scans the specimen 100 with a spot formed by the illuminating optical system.

The collector 109 includes a lens, collects light that is scattered or reflected from the specimen 100, and converges the collected light onto the detection surface of the detector 108. The detecting optical system may include one lens or a plurality (two or more) of lenses. Part or the whole of the detecting optical system maybe an optical component that totally reflects the light or reflects part of the light. The optical component may include, for example, a mirror, an elliptical mirror, and a semitransparent mirror.

The detector 108 converts the light collected by the collector 109 to an electric signal according to its intensity, and outputs the electric signal as a detection signal. The amplifier 107 receives the detection signal from the detector 108, and amplifies the signal at a previously set amplification factor. The A/D converter 106 converts the amplified signal to a digital signal so that it matches the data form in the PC 105. The PC 105 processes the data received from the A/D converter 106, and outputs the position and size of a defect on the specimen 100.

(2-2) The Configuration Example of the Beam Formation Unit 102

Figure 2:
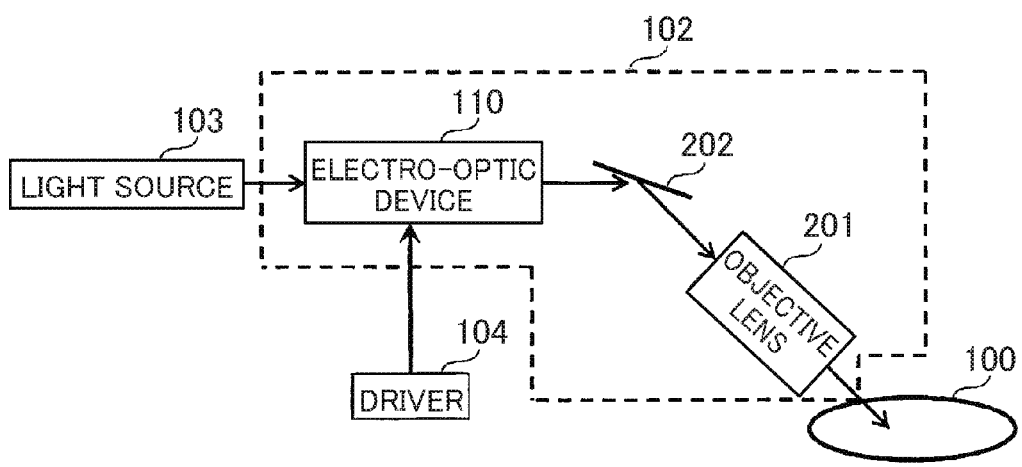
FIG. 2 is a diagram of assistance in explaining the configuration around an electro-optic device.

FIG. 2 illustrates the configuration example of the optical system adopted for switching the polarization state of the illumination light during the inspection. FIG. 2 represents the illuminating optical system around the electro-optic device 110 that is disposed in the beam formation unit 102. The switching of the polarization state is executed based on a control signal from the PC 105. Specifically, by the control signal, the voltage applied from the driver 104 to the electro-optic device 110 is switched at an appropriate timing and time interval (for example, FIGS. 7, 9, and 10). As described above, the optical inspection device 1 often uses an S-polarization state and a P-polarization state.

The light that has passed through the electro-optic device 110 is directed toward the specimen 100 by a mirror 202 and the like, and is collected into a desired illumination shape by an objective lens 201, so that the specimen 100 is irradiated with the light. Hereinafter, unless otherwise specified, the polarization direction of the light in the preceding stage of the electro-optic device 110 and the crystal axis direction of the electro-optic device 110 are determined so as to create two types of linearly polarized states orthogonal to each other in the subsequent stage of the electro-optic device 110 when the voltage applied by the driver 104 is changed.

(2-3) The Inspection Operation with the Switching of Polarization

Figure 3:
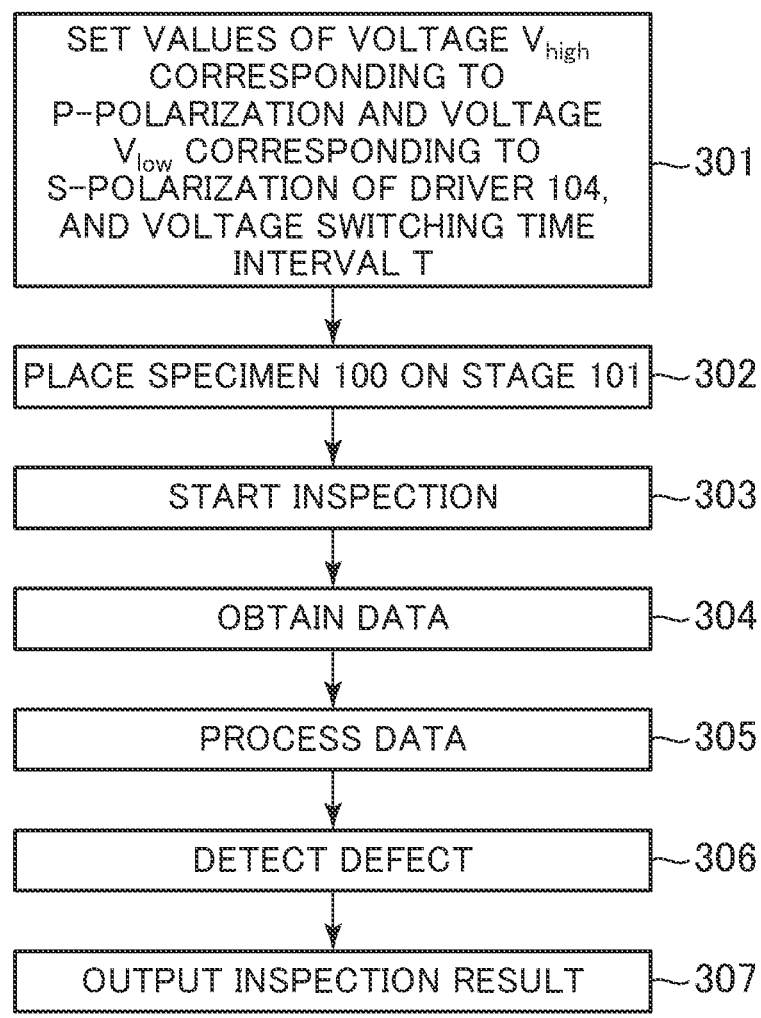
FIG. 3 is a flowchart of assistance in explaining a processing procedure during inspection.

FIG. 3 illustrates a processing operation in the case of performing the inspection while the illumination light with which the specimen 100 is illuminated is switched to the S-polarization state or the P-polarization state.

(Step 301)

In the device adjustment stage, the PC 105 sets the value of voltage $V_{high}$ corresponding to the P-polarization state of the driver 104, the value of voltage $V_{low}$ corresponding to the S-polarization state of the driver 104, and voltage switching time interval T. These values are instructed to the PC 105 by the operator through GUI displayed on, for example, a display unit, not illustrated. Of course, these values may be previously stored in the device.

(Steps 302 to 304)

After the specimen 100 is placed on the stage 101, the PC 105 starts the inspection to obtain data. During the inspection, the entire surface of the specimen 100 is scanned with the illumination light whose polarization state is switched in a time division manner. In this embodiment, the switching of the polarization state is controlled by the PC 105 so that the entire surface of the inspection region is irradiated with both of the spot in the P-polarization state and the spot in the S-polarization state. Data is obtained by detecting scattered light from a defect by the detector 108 and by digital-converting its detection result.

(Steps 305 to 307)

The PC 105 executes predetermined data processing based on the obtained data, and detects the presence or absence of a defect. In addition, the PC 105 calculates the size and coordinates of a defect on the specimen 100, and outputs the inspection result. For the data processing, an existing technique is used.

(2-4) The Operation Condition Required during the Inspection

The value of the voltage applied from the driver 104 to the electro-optic device 110 is required to be determined so that the polarization state of the illumination light is switched between the P-polarization state and the S-polarization state. The time to switch the voltage is set according to the inspection method. Switching time interval T may be synchronous with a fixed value, or the repetition frequency of the light source 103, or the operation of the stage 101.

For example, the polarization state may be switched at timing such as for one pulse, every two pulses, and every three pulses of the illumination light outputted from the light source 103. In addition, the polarization state may be switched at timing such as each time the stage 101 makes one rotation, half rotation, and ½ rotation. During the data processing, the data obtained in the S-polarization state and the data obtained in the P-polarization state may be integrated, and one data processing result may be outputted. In this case, both of a defect that can be detected only in the S-polarization and a defect that can be detected only in the P-polarization can be detected. Thus, defect missing can be reduced.

In addition, the data obtained in the S-polarization state and the data obtained in the P-polarization state may be separated, the data processing may be executed with respect to each of them, and two data processing results maybe independently outputted. At this time, the data-processing methods with respect to the respective one of two pieces of data maybe similar to the other or different from each other. By optimizing the contents of the data processing according to the two polarization states, the sensitivity can be improved. In this case, the missing of a defect that can be detected only in one of the S-polarization and the P-polarization can be reduced, and in some cases, the type of a defect can be estimated by comparing two results.

Figure 4:
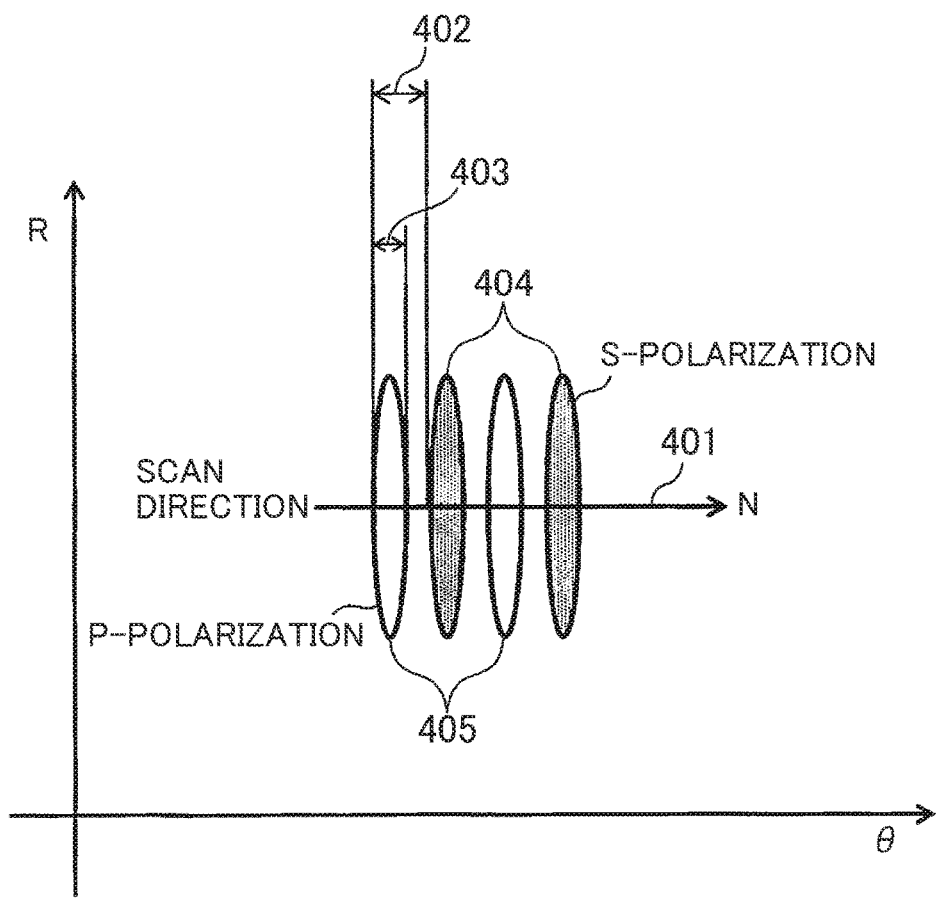
FIG. 4 is a conceptual diagram of assistance in explaining a scanning method by which the polarization state is switched for each pulse.

FIG. 4 illustrates the scanning method of the specimen 100 when the inspection is performed while the S-polarization state and the P-polarization state are switched for each pulse of the illumination light. The stage 101 rotates while holding the specimen 100 on its placing surface. Each time the stage 101 allows the specimen 100 to make one rotation, the stage 101 translationally moves in the radius direction of the specimen 100 by a certain feed pitch. The translational movement direction may be the direction of the inner periphery from the outer periphery of the specimen 100, or the direction of the outer periphery from the inner periphery of the specimen 100. The translational movement direction of the stage 101 is the R direction, and the rotation direction of the stage is the θ direction.

In FIG. 4, the position through which the center of the illumination spot passes in the inspection of an Nth track is indicated by an arrow 401. By switching the polarization for each pulse of the illumination light, the surface of the specimen can be inspected under both of the conditions of the S-polarization and the P-polarization during one inspection. The ellipses in the drawing represent the inspection regions of the specimen 100 by spots 404 in the S-polarization, and the inspection regions of the specimen 100 by illumination spots 405 in the P-polarization. At this time, to complete the inspection in one scan operation, the entire surface of the specimen 100 is required to be scanned at least once or more with the illumination spot in each of the S-polarization and the P-polarization. For that, a distance 402 between the spots is required to be set to be equal to or less than half of a size 403 in the scan direction of the pulse.

Figure 5:
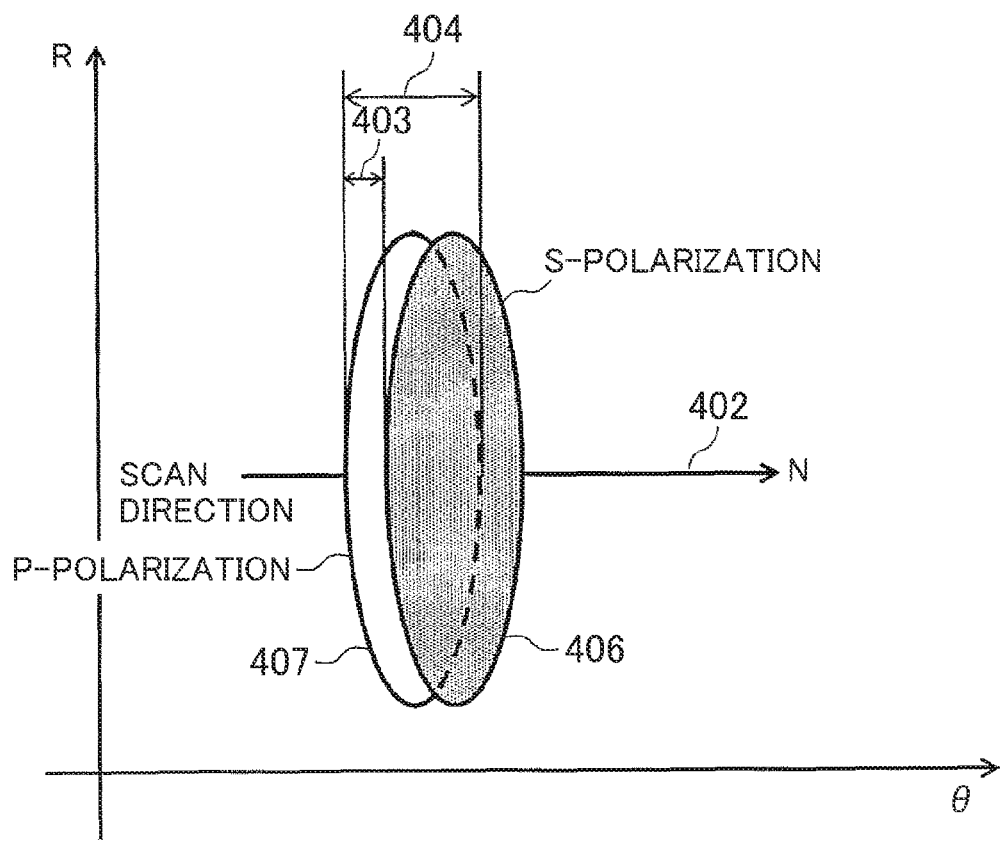
FIG. 5 is an enlarged view of assistance in explaining the specific example of the scanning method by which the polarization state is switched for each pulse.

FIG. 5 illustrates an enlarged view of a spot 406 in the S-polarization and an illumination spot 407 in the P-polarization. In FIG. 4, for visibility, the spot 406 in the S-polarization and the illumination spot 407 in the P-polarization are illustrated so as not to overlap. Actually, as illustrated in FIG. 5, the spot 406 in the S-polarization and the illumination spot 407 in the P-polarization overlap considerably.

(2-5) The GUI Setting Screen

Figure 6:
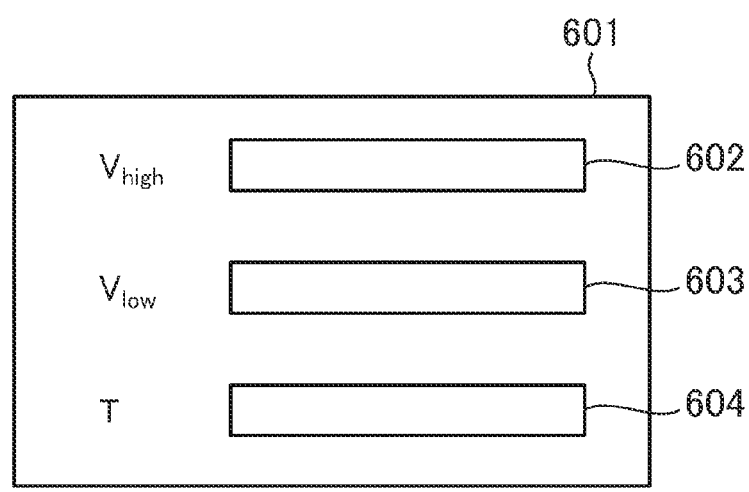
FIG. 6 is a diagram illustrating an example of a GUI screen used for setting a driver.

FIG. 6 illustrates an example of a GUI screen 601 operated by the operator for controlling the electro-optic device 110. To input boxes 602 and 603, the values of the voltages applied by the driver 104 are designated. The values of the voltages here are the value of the voltage applied by the driver 104 for irradiating the specimen 100 with the illumination light in the S-polarization, and the value of the voltage applied by the driver 104 for irradiating the specimen 100 with the illumination light in the P-polarization. Now, when the relation between the polarization direction and the voltage is held in the optical inspection device 1 (PC105), only the polarization states in the S-polarization and the P-polarization may be designated through the input boxes 602 and 603.

To an input box 604, the switching timing is designated. For example, the switching time is designated. When the correspondence relation between the switching time and the switching reference is held in the optical inspection device 1 (PC 105), the switching reference, such as "for each track" and "for each pulse of illumination", may be designatable through the input box 604. The correspondence relation here may be a fixed value, or the repetition frequency of the illumination light, or the rotation of the stage. It is to be noted that the values designated through the input boxes 602, 603, and 604 may be provided to the illuminating optical system.

Figure 7:
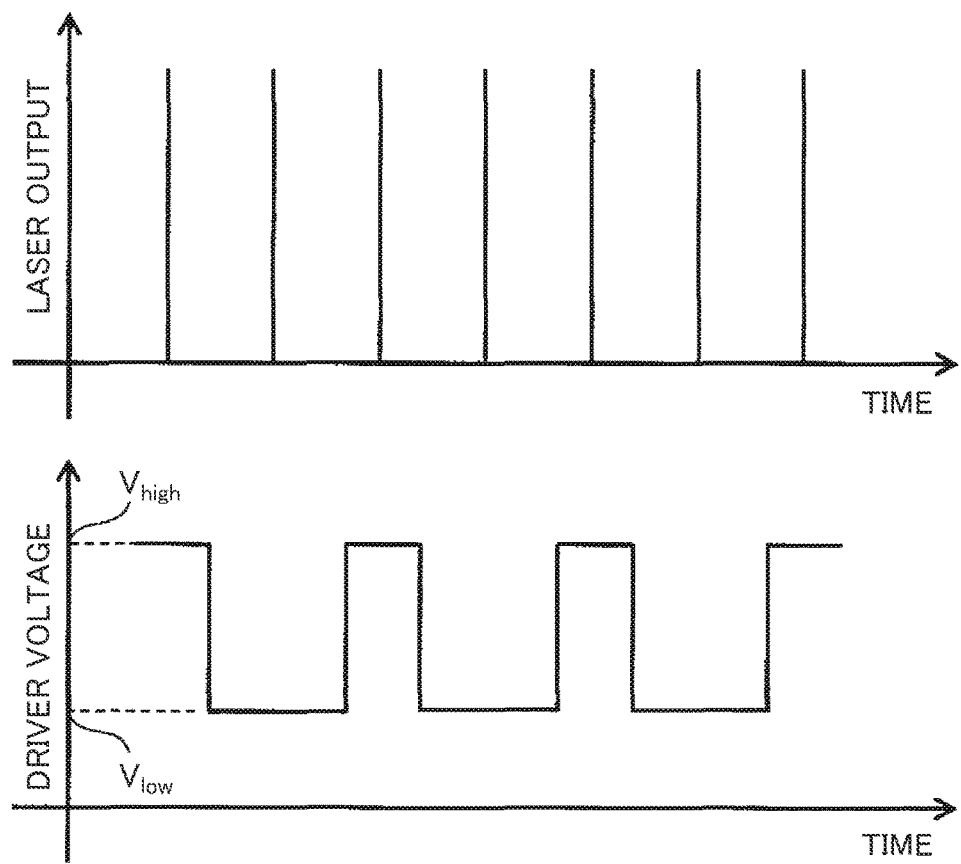
FIG. 7 is a diagram of assistance in explaining the relation between the laser output timing and the driver voltage switching timing.

(2-6) The Relation between the Laser Output Timing and the Driver Voltage Switching Timing FIG. 7 illustrates the relation between the output timing of the illumination light (here, laser) from the light source 103 and the driver voltage switching timing. The laser oscillates pulses, and outputs the pulses at a constant time interval. To switch the polarization for each pulse, it is necessary to switch between voltage $V_{high}$ corresponding to the P-polarization and voltage $V_{low}$ corresponding to the S-polarization during the period in which the light source 103 does not output the laser. It is to be noted that the pulse interval of the laser is determined so that a spot formed by the outputted laser satisfies the condition in FIG. 5.

(2-7) Summary

In the optical inspection device 1 according to this embodiment, the entire surface of the specimen 100 is illuminated with each of the plurality of illumination lights having the polarization states different from each other during one inspection. Thus, the throughput is not lowered.

It is to be noted that in the above description, the polarization to be switched includes the S-polarization and the P-polarization, but by adjusting the voltage applied from the driver 104 to the electro-optic device 110, polarization other than these (for example, circular polarization and elliptical polarization) can also be switched. In addition, in the above description, two polarization conditions of the S-polarization and the P-polarization are switched, but three or more polarization conditions may be switched. At this time, in order that the entire surface of the specimen 100 can be inspected with the spots under all the polarization conditions once or more, it is necessary to sufficiently take the portion in which the spots corresponding to the polarization conditions overlap with each other. When M polarization conditions are switched, the distance 403 between the spots is required to be set to be equal to or less than 1/M of the size 404 in the scan direction of the pulse. However, even when the number of polarization conditions for the inspection is increased, hardware change such as optical device addition is not required.

(3) Second Embodiment

Figure 8:
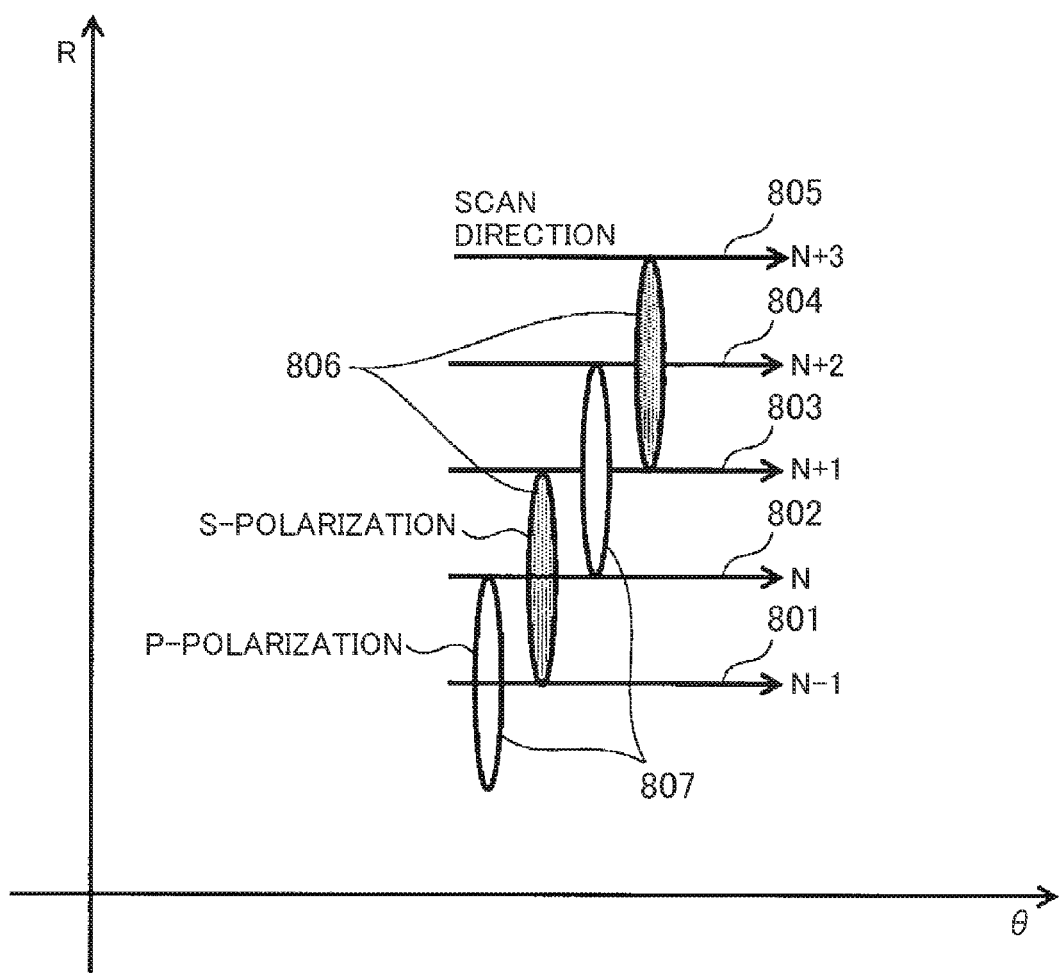
FIG. 8 is a conceptual diagram of assistance in explaining a scanning method by which the polarization state is switched for each track.

In the above embodiment, the case of switching the S-polarization state and the P-polarization state for each pulse of the illumination light for the inspection has been described. Here, the case of switching the S-polarization state and the P-polarization state for each track will be described. FIG. 8 illustrates a polarization state switching method in this embodiment.

Also in this embodiment, the stage 101 rotates while holding the specimen 100 on its placing surface. Each time the stage 101 allows the specimen 100 to make one rotation, the stage 101 translationally moves in the radius direction of the specimen 100 by a certain feed pitch. The translational movement direction may be the direction of the inner periphery from the outer periphery of the specimen 100, or the direction of the outer periphery from the inner periphery of the specimen 100. Also, here, the translational movement direction of the stage 101 is the R direction, and the rotation direction of the stage is the θ direction.

In this embodiment, as illustrated in FIG. 8, the polarization state of the illumination light is switched at timing at which the stage 101 performs the translational movement. Due to this, the polarization state of the illumination light on the Nth track and the polarization state of the illumination light on the (N+1)th track are different from each other. In FIG. 8, spots 806 on the Nth track and the (N+2)th track are scanned with the illumination light in the S-polarization state, and spots 807 on the (N−1)th track and the (N+1)th track are scanned with the illumination light in the P-polarization state. An arrow 801 in the drawing represents the track at the center position of the spot 807 for inspecting the (N−1) th track. Likewise, an arrow 802 represents the track at the center position of the spot for inspecting the Nth track, an arrow 803 represents the track at the center position of the spot for inspecting the (N+1) th track, an arrow 804 represents the track at the center position of the spot for inspecting the (N+2)th track, and an arrow 805 represents the track at the center position of the spot for inspecting the (N+3)th track.

To complete the inspection in one scan operation, the entire surface of the specimen 100 is required to be scanned at least once or more with the illumination spot in each of the S-polarization and the P-polarization. For this, the feed pitch of the stage is required to be equal to or less than half of the size in the R direction of the spot.

In the optical inspection device 1 according to this embodiment, the entire surface of the specimen 100 is illuminated with each of the illumination lights having the polarization states different from each other during one inspection. Thus, the throughput is not lowered.

Also in this embodiment, three or more polarization conditions may be switched during one inspection. At this time, in order that the entire surface of the specimen 100 can be inspected with the spots under all the polarization conditions once or more, it is necessary to sufficiently take the portion in which the spots corresponding to the polarization conditions overlap with each other. When M polarization conditions are switched, the feed pitch of the stage is required to be set to be equal to or less than 1/M of the size in the R direction of the spot.

(4) Third Embodiment

Figure 9:
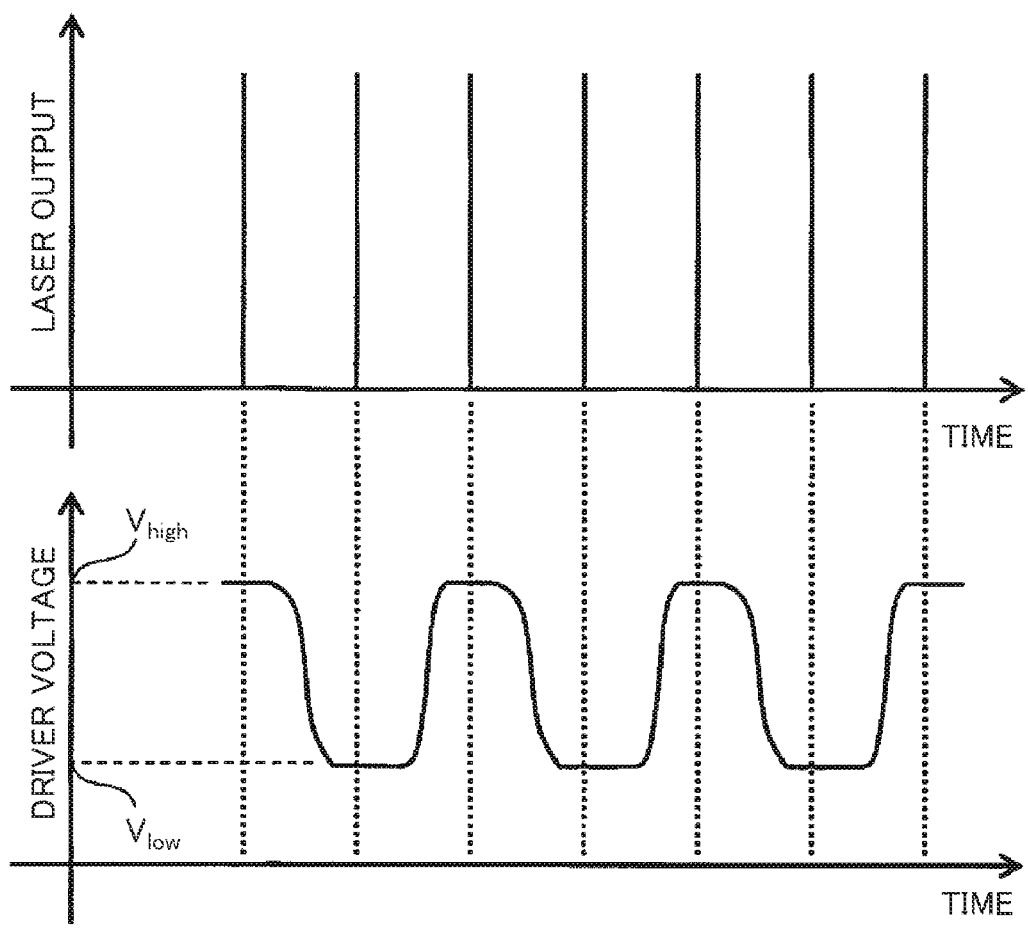
FIG. 9 is a diagram of assistance in explaining the relation between the laser output timing and the driver voltage switching timing when there is waveform dullness at the time of driver voltage switching.

Here, the more preferable relation between the laser output timing and the driver voltage switching timing will be described. In FIG. 7 used in the description of the first embodiment, it is assumed that the driver voltage waveform ideally changes. However, when the driver 104 is operated at high speed (or when the voltage switching frequency becomes high), dullness appears in the output voltage of the driver 104, as illustrated in FIG. 9. That is, due to the response speed of the driver 104, the dullness of the waveform at the time of the switching of $V_{high}$ and Vlow is significant. Accordingly, in this embodiment, the voltage switching timing by the PC 105 is set so that the switching of $V_{high}$ and $V_{low}$ is completed during the laser output.

Figure 10:
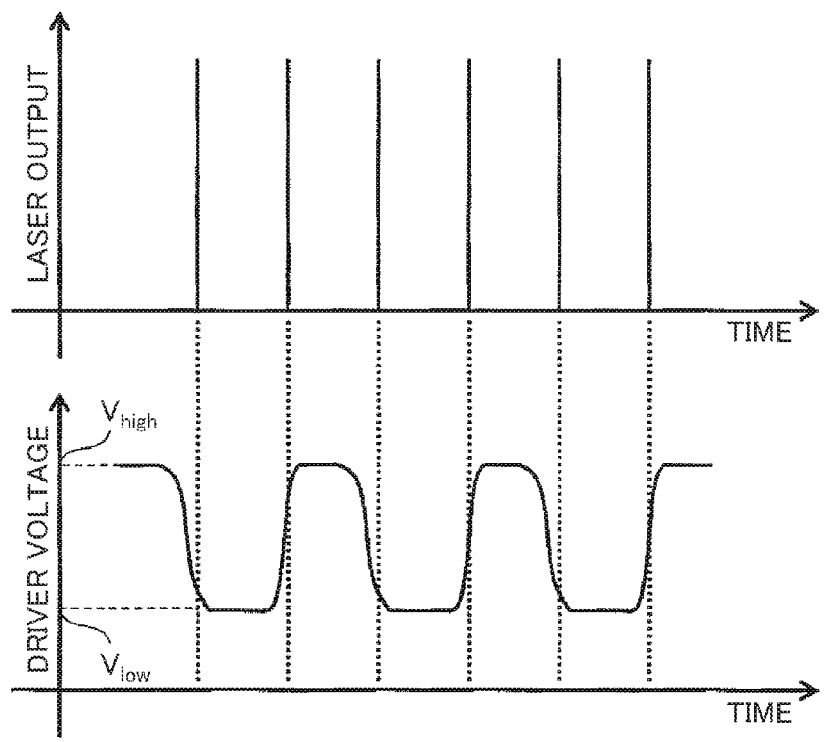
FIG. 10 is a diagram of assistance in explaining the case where the laser output timing and the driver voltage switching timing deviate from the appropriate timing.

FIG. 10 illustrates the case where the laser output timing and the driver voltage switching timing deviate from the appropriate timing. In FIG. 10, since the laser is outputted during the switching of $V_{high}$ and $V_{low}$ (during transition), the specimen 100 cannot be irradiated with the illumination light in a desired polarization state. Accordingly, in this embodiment, the driver voltage switching timing by the PC 105 is adjusted so as to be the appropriate timing with respect to the laser output timing. It is to be noted that when the polarization of the illumination light cannot be switched well only by the adjustment of the driver voltage timing, the repetition frequency of the laser and time interval T to switch the polarization state are required to be appropriately set.

(5) Fourth Embodiment

Figure 11:
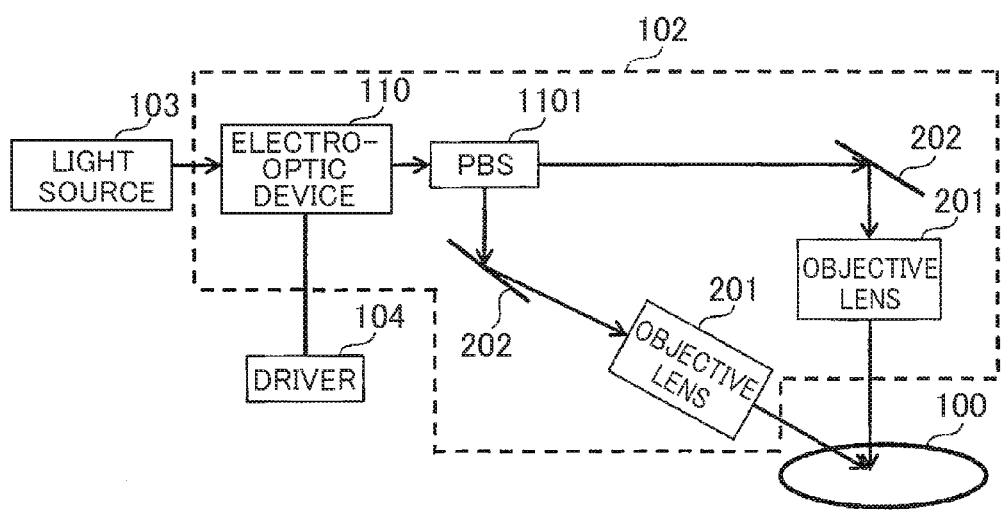
FIG. 11 is a diagram of assistance in explaining the configuration around the electro-optic device corresponding to an inspection method that can switch the illumination direction.

In the first embodiment, the polarization state of the illumination light is switched between the S-polarization state and the P-polarization state. In this embodiment, the case where the irradiation angle of the illumination light with respect to the specimen 100 is switched will be described. FIG. 11 illustrates the configuration of the optical system adopted in this embodiment. In this embodiment, the switching of the irradiation angle of the illumination light is achieved through the control of the electro-optic device 110. In FIG. 11, the portions corresponding to FIG. 2 are indicated by similar reference signs.

In this embodiment, a polarizing beam splitter (PBS) 1101 is disposed in the subsequent stage of the electro-optic device 110, and the mirror 202 and the objective lens 201 are disposed for each of two split illumination lights. The polarizing beam splitter 1101 is an optical device that splits the inputted light into the component of the light oscillating in a certain direction and the component of the light oscillating in the direction orthogonal thereto. Specifically, the polarizing beam splitter 1101 splits the light into two paths by passing the light having one polarization component while reflecting the light having the other polarization component.

The PC 105 in this embodiment also switches the voltage applied to the electro-optic device 110 to switching-control the polarization direction of the irradiation light that is outputted from the electro-optic device 110. That is, the polarization state of the light inputted to the polarizing beam splitter 1101 is switched. The travel direction of the light that is outputted from the polarizing beam splitter 1101 is switched in synchronization with the switching of the polarization direction of the light.

Both of the lights that have been switched in the two directions change their directions to the specimen 100 by the mirrors 202, so that the specimen 100 is irradiated with the lights through the objective lenses 201, and a desired spot shape is then formed. The irradiation angle of the illumination light with respect to the specimen 100 can be freely set according to the disposition of the mirror 202 and the objective lens 201, but in the semiconductor inspection, the irradiation angle is often set to 0° or near 80°. Hereinafter, the input angle of 0° with respect to the surface of the specimen 100 is referred to as "vertical", and the input angle of near 80° with respect to the surface of the specimen 100 is referred to as "oblique".

In this embodiment, the voltage values of the driver 104 corresponding to the "vertical" and the "oblique" are set to the input box 602 of $V_{high}$ and the input box 603 of $V_{low}$ on the GUI illustrated in FIG. 6. In this case, the PC 105 may integrate the data obtained for the light that is vertically inputted to the specimen 100 and the data obtained for the light that is obliquely inputted to the specimen 100, execute the data processing (step 305), and output the inspection result (step 307).

When the optical inspection device 1 according to this embodiment is used, it is possible to detect both of a defect that can be detected only with the inputted light in the "vertical" direction and a defect that can be detected only with the inputted light in the "oblique" direction. Thus, defect missing can be reduced. Of course, the switching of the "vertical" direction and the "oblique" direction is executed in a time division manner. In addition, the input direction switching timing is the same as the laser output timing and the driver voltage switching timing according to the above embodiments.

In the above description, the data detected for the inputted light in the "oblique" direction and the data detected for the inputted light in the "vertical" direction are integrated. However, these two data pieces may be separated, the data processing may be executed with respect to each of them (step 305), and two independent inspection results may be outputted (step 307). In this case, the processing with respect to the two data pieces (step 304) may be performed similarly or differently. By optimizing the contents of the data processing according to the illumination angle, the sensitivity can be improved. In this case, the missing of a defect that can be detected only by one of the inputted light in the "oblique" direction and the inputted light in the "vertical" direction can be reduced, and in some cases, the type of a defect can be estimated by comparing two results.

(6) Fifth Embodiment

In this embodiment, the case where the power of the illumination light, not the polarization and irradiation angle of the illumination light, is switched in a time division manner during one inspection will be described. As described above, the optical inspection device 1 estimates the size of a defect from the amount of scattered light. Since intent scattered light is generated from a sufficiently large defect, the output of the detector 108 can be saturated. When the output of the detector 108 is saturated, the precise amount of the scattered light is not found. Consequently, the size of the defect cannot be precisely estimated.

Accordingly, in this embodiment, by executing, in a time division manner, the inspection at low power in which the output of the detector 108 is not likely to be saturated and the inspection at the typical power, the dynamic range of the detector 108 is increased without significantly lowering the throughput. This can estimate the size of even a larger defect than the conventional technique.

Figures 12, 13:
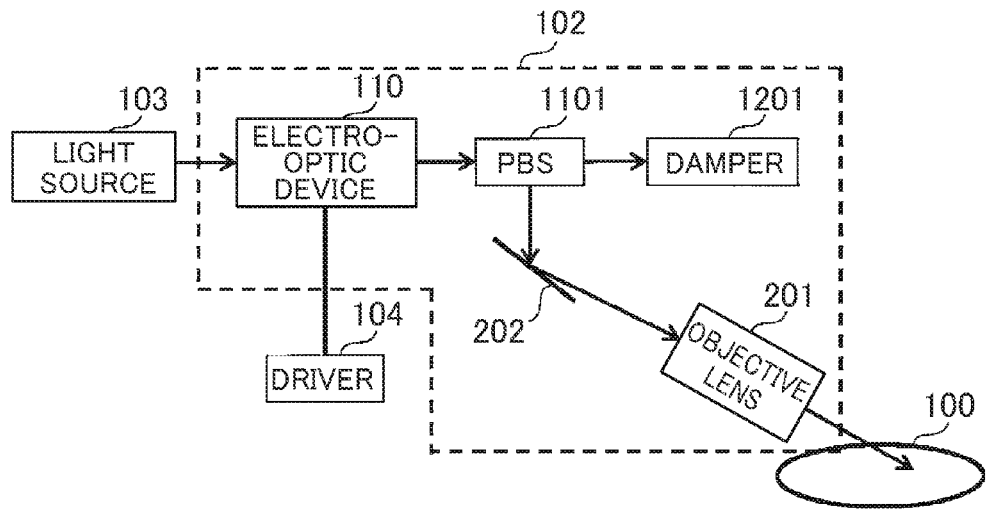
FIG. 12 is a diagram of assistance in explaining the configuration around the electro-optic device corresponding to an inspection method that can switch the illumination power.
FIG. 13 is a table of assistance in explaining the correspondence relations between the adjustment of the polarization states by the electro-optic device and the powers (transmissivities).

FIG. 12 illustrates the configuration example of the optical system adopted in this embodiment. In this embodiment, the power of the illumination light that is inputted to the specimen 100 is switched through the control of the electro-optic device 110. It is to be noted that in FIG. 12, the portions corresponding to FIG. 11 are indicated by similar reference signs. Like the above embodiments, the PC 105 also adjusts the voltage applied to the electro-optic device 110 to adjust the rates of two polarization components included in the irradiation light that is outputted from the electro-optic device 110.

Also in this embodiment, there are two travel directions of the split lights. A damper 1201 is disposed in one of the travel directions. The light that is inputted to the damper 1201 is not used for the inspection. The disposition of the damper 1201 can reduce unpreferable light generation. The specimen 100 is illuminated with the other light split by the polarizing beam splitter 1101 through the mirror 202 and the objective lens 201.

By controlling the light polarization state by the electro-optic device 110, it is possible to adjust the power of the illumination light transmitting through or reflecting on the polarizing beam splitter 1101 and with which the specimen 100 is irradiated. FIG. 13 illustrates the relations between the polarization states caused by the control of the electro-optic device 110 and the amounts of lights that transmit through the polarizing beam splitter 1101. The oscillation direction of the light that transmits through the polarizing beam splitter 1101 is different according to the method of disposing the polarizing beam splitter 1101 with respect to the inputted light. Thus, FIG. 13 is an example.

Each of the double-headed arrows in FIG. 13 indicates a light oscillation direction. In addition, the length of each of the double-headed arrows represents the magnitude of the amount of light transmitted. All of the polarization states are linear polarization in the subsequent stage of the polarizing beam splitter 1101, so that the transmissivities (powers) are modulated. This phenomenon is not dependent on the disposition of the polarizing beam splitter 1101. When the output of the detector 108 is not saturated at the power equivalent to the typical inspection, the output obtained by the inspection at the power equivalent to the typical inspection is adopted. On the other hand, when the output of the detector 108 is not saturated in the inspection at low power (power lower than the typical inspection), the PC 105 estimates the amount of scattered light in the inspection at the power equivalent to the typical inspection based on the output of the detector 108 at low power.

In this embodiment, for example, as the polarization state in which the power of the typical inspection is obtained, the P-polarization state in which a transmissivity of 100% is obtained is used, and as the polarization state in which the low power is obtained, the circular polarization in which a transmissivity of 50% is obtained is used. Of course, these are an example, and the switching between other transmissivities maybe used, the switching between three or more types of transmissivities may be used, and continuous transmissivity switching may be used.

Like this embodiment, the power of the irradiation light used for the inspection is switched through the adjustment of the polarization state by the control of the electro-optic device 110. Thus, even a larger defect can be inspected, as compared with the case where the inspection is performed without switching the power. It is to be noted that the PC 105 may be provided with the function of controlling the amount of the adjustment of the polarization state by the electro-optic device 110 (or of further lowering the power) according to whether the output of the detector 108 is saturated.

Also in this embodiment, three or more power conditions may be switched during one inspection. At this time, the dynamic range of the detector 108 can be further widened, as compared with the case where two power conditions are switched. In addition, even when the number of power conditions for the inspection is increased, hardware change such as optical device addition is not required.

(7) Sixth Embodiment

None of the above embodiments is limited to one detector 108 and one collector 109, and a plurality of detectors 108 and a plurality of collectors 109 may be used. When the plurality of detectors 108 and the plurality of collectors 109 are disposed, the spatial distribution of generated scattered light can be estimated. For example, with respect to the outputs of the detectors 108, the data processing (step 305) and the defect detection (step 306) may be individually executed, and a plurality of inspection results may be outputted (step 307). Some defect shapes and defect types have different scattered light spatial distributions, so that by comparing these, the defect types and the defect shapes can be estimated. Further, a larger number of defect types can be estimated by combining the spatial distribution of scattered light and inspection results in the plurality of polarization states described in the first embodiment or inspection results in the plurality of illumination directions described in the fourth embodiment, as compared with the case of not combining.

In this case, the outputs of the plurality of detectors 108 may be integrated, and with respect to the integrated data, the data processing (step 305), the defect detection (step 306), and the inspection result output (step 307) may be executed. By integrating the outputs of the plurality of detectors 108, noise that is randomly caused in the outputs of the detectors 108 can be reduced, and higher sensitive inspection can be performed, as compared with the case where there are only one detector 108 and only one collector 109.

Further, when the plurality of detectors 108 and the plurality of collectors 109 are used, the dynamic range of the detectors 108 can be increased. Since scattered light from a defect has a spatial distribution, all of the outputs of the plurality of detectors 108 are not saturated at the same time in many cases. When some of the outputs of the plurality of detectors 108 are saturated, only the outputs of the unsaturated detectors 108, not the outputs of the saturated detectors 108, are adopted. This can precisely estimate the amount of scattered light. At this time, the dynamic range of the detectors 108 can be increased, as compared with the case where only one detector 108 and only one collector 109 are used. This can estimate the size of even a larger defect. By combining this with the power switching function described in the fifth embodiment, the size of an estimable defect can be further increased. However, when only one detector 108 and only one collector 109 are used, the number of components of the device is reduced, as compared with the case where there are the plurality of them. This can manufacture the device at lower cost.

LIST OF REFERENCE SIGNS

1 . . . Optical inspection device
100 . . . Specimen
101 . . . Stage
102 . . . Beam formation unit
103 . . . Light source
104 . . . Driver
105 . . . PC
106 . . . A/D converter
107 . . . Amplifier
108 . . . Detector
109 . . . Collector
110 . . . Electro-optic device
111 . . . Semitransparent mirror
112 . . . Detector
201 . . . Objective lens
202 . . . Mirror
601 . . . GUI screen
602, 603, 604 . . . Input box
1101 . . . Polarizing beam splitter
1201 . . . Damper

The invention claimed is:

1. An inspection device comprising:
an illuminating optical unit that irradiates a discretionary region of a specimen with light;
a control unit that gives instructions to the illuminating optical unit; and
at least one detection unit that detects light from the specimen,
wherein the illuminating optical unit includes a light source unit that generates light, and an electro-optic device unit to which the light generated by the light source unit is inputted, and
wherein, based on the instructions from the control unit, the electro-optic device unit adjusts the light to be in a desired polarization state, the light having been generated by the light source unit, and irradiates the specimen with the light,
wherein the electro-optic device unit adjusts a polarization state of the light inputted from the light source according to a voltage instructed from the control unit, and
wherein the voltage includes a voltage corresponding to P-polarization and a voltage corresponding to S-polarization.

2. The inspection device according to claim 1, further comprising a display unit to which the value of the voltage and the timing at which the voltage is switched can be inputted as an instruction input with respect to the control unit or the illuminating optical unit.

3. The inspection device according to claim 1,
wherein the electro-optic device unit includes:
a split unit that splits the light with which the specimen is irradiated; and
a split light irradiation unit that irradiates the specimen with the split lights at input angles different from each other.

4. The inspection device according to claim 1,
wherein the electro-optic device unit includes:
a split unit that splits the light with which the specimen is irradiated; and
a split light irradiation unit that irradiates the specimen with one of the split lights.

5. An inspection device comprising:
an illuminating optical unit that irradiates a discretionary region of a specimen with light;
a control unit that gives instructions to the illuminating optical unit; and
at least one detection unit that detects light from the specimen, wherein the illuminating optical unit includes a light source unit that generates light, and an electro-optic device unit to which the light generated by the light source unit is inputted, wherein, based on the instructions from the control unit, the electro-optic device unit adjusts the light to be in a desired polarization state, the light having been generated by the light source unit, and irradiates the specimen with the light, and wherein the electro-optic device unit adjusts a polarization state of the light inputted from the light source according to timing instructed from the control unit.

6. The inspection device according to claim 5, wherein the control unit instructs the timing based on a repetition frequency of the light generated by the light source unit.

7. The inspection device according to claim 6, wherein the timing is timing at which the light from the light source unit is not inputted to the electro-optic device unit.

8. The inspection device according to claim 7, wherein the timing is set so as not to overlap a time interval at which the voltage is changed when the electro-optic device unit switches the voltage by the instruction from the control unit and the timing of the repetition frequency.

9. The inspection device according to claim 6, wherein the control unit switches the polarization state of the light inputted from the light source to an S-polarization state or a P-polarization state at the timing based on the repetition frequency of the light, and wherein an interval between a region irradiated in the S-polarization state and a region located adjacent to the region and irradiated in the P-polarization state is equal to or less than half of a distance in a scan direction of the region irradiated in one of the S-polarization state and the P-polarization state.

10. The inspection device according to claim 5, wherein the control unit instructs the timing for scanning the specimen over a plurality of tracks.

11. The inspection device according to claim 10, wherein a feed pitch in a translational movement direction of a stage that can rotate and translationally move holding the specimen is equal to or less than half of the size of the region irradiated with the light in the translational movement direction.

12. The inspection device according to claim 5, wherein the control unit instructs the timing based on the operation of the stage that rotates holding the specimen.

\* \* \* \* \*